United States Patent [19]

Krüger et al.

[11] Patent Number: 4,873,252
[45] Date of Patent: Oct. 10, 1989

[54] ACYLATED AMINOALCOHOLS FOR REPELLING INSECTS AND MITES

[75] Inventors: Bernd-Wieland Krüger, Wuppertal; Klaus Sasse, Bergisch-Gladbach; Franz-Peter Hoever; Günther Nentwig, both of Cologne; Wolfgang Berhrenz, Overath, all of Fed. Rep. of Germany

[73] Assignee: Bayer Aktiengesellschaft, Leverkusen, Fed. Rep. of Germany

[21] Appl. No.: 165,684

[22] Filed: Mar. 9, 1988

[30] Foreign Application Priority Data

Mar. 12, 1987 [DE] Fed. Rep. of Germany ....... 3708033

[51] Int. Cl.$^4$ .................... A01N 43/40; C07D 211/22
[52] U.S. Cl. ..................................... 514/315; 546/245
[58] Field of Search ......................... 546/245; 514/315

[56] References Cited

U.S. PATENT DOCUMENTS 3,178,439  4/1965  Cislak .................................. 546/245
4,298,612 11/1981  McGovern et al. ................. 514/319

FOREIGN PATENT DOCUMENTS 3106877  2/1982  Fed. Rep. of Germany .
 646581 12/1984  Switzerland .
1604855 12/1981  United Kingdom .

OTHER PUBLICATIONS

K. H. Büchel, *Chemistry of Plant Protection Agents and Agents for Combating Pests*, vol. I, R. Wegler (editor), Springer Verlage, Berlin, 1970, pp. 487–496.

Chapman, J., *Tetrahedron Letters*, No. 1, pp. 113–119 (1966).

Ferri, C., *Reactions of Organics Synthesis*, George Thieme Verlag, Stuttgart, 1978, pp. 496–497.

Kochhar, R. et al., *Indian J. Med. Res.* 62, 1, Jan. 1974.

*Chemical Abstracts*, 83:205719u (1975), [Japan Kokai 75,106,920, Mizuno et al., 8/22/75].

Primary Examiner—Richard A. Schwartz
Attorney, Agent, or Firm—Sprung Horn Kramer & Woods

[57] ABSTRACT

Repelling insects and mites with acylated α,ω-aminoalcohol derivatives of the formula

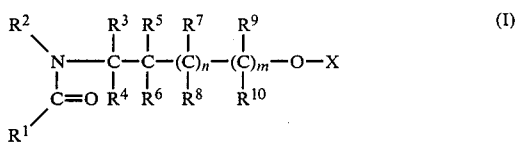

in which
  X represents hydrogen, $COR^{11}$, $COOR^{12}$ or $R^{13}$,
  $R^1$ represents optionally substituted alkyl or alkenyl radicals,
  $R^2$, $R^{11}$ and $R^{13}$ are identical or different and represent optionally substituted alkyl or alkenyl radicals,
  $R^3$ to $R^{10}$ are identical or different and represent hydrogen, or represent optionally substituted alkyl radicals, and wherein
  $R^2$ and $R^3$, together with the atoms to which they are bonded, can also form an optionally substituted monocyclic ring, and n and m are identical or different and denote 0 or 1, with the proviso that X does not represent hydrogen or $R^{13}$ if n and m represent 0.

Those compounds wherein $R^2$ and $R^3$ together are —(CH$_2$)$_4$— and $R^1$ is C$_2$–C$_6$-alkyl or C$_3$–C$_6$-alkenyl are new.

7 Claims, No Drawings

ACYLATED AMINOALCOHOLS FOR REPELLING INSECTS AND MITES

The present invention relates to the use of acylated α,ω-aminoalcohol derivatives, some of which are known, as insect- and mite-repellent agents.

Agents which repel insects and mites (repellents) have the task of preventing harmful or troublesome arthrapods from coming into contact with and from stinging and sucking or biting surfaces which attract them, for example the skin of animals and humans, if these have not first been treated with such agents.

Numerous active compounds have already been proposed as repellents. (Compare, for example, K. H. Büchel in Chemie der Pflanzenschutz- und Schädlingsbekämpfungsmittel (Chemistry of the Plant Protection Agents and Agents for combating Pests); published by: R. Wegler, Volume 1, Springer Verlag Berlin, Heidelberg, N.Y., 1970 page 487 et seq.).

3-Methyl-benzoic acid diethylamide (DEET), dimethyl phthalate and 2-ethyl-hexane-1,3-diol are known in particular and have been used for a relatively long time, and of these above all DEET has achieved considerable importance in practice (see, for example, R. K. Kocher, R. S. Dixit, C. I. Somaya; Indian J. Med. Res. 62, 1 (1974)):

A considerable disadvantage of the known repellents is that their presistent action in some cases lasts only a relatively short time (only a few hours).

Some of the compunds defined by the following formula (I) are known.

Corresponding polyhydroxyamines are known, for example, from Chemical Abstracts 83 (25): 205/791.

N-Alkanoyl- and alkenoyl-hydroxyalkylpiperidines are furthermore known from U.S. Pat. No. 3,178,439. Other piperidines are known from Tetrahedron Lett. No. 1 (1966) pages 113–119.

However, nothing has as yet been disclosed of an insect- and mite-repellent action of these compounds.

It has now been found that the acylated α,ω-aminoalcohol derivatives, some of which are known, of the formula I

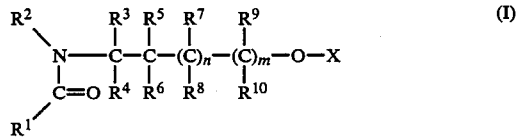

in which
X represents hydrogen, $COR^{11}$, $COOR^{12}$ or $R^{13}$,
$R^1$ represents optionally substituted alkyl or alkenyl radicals,
$R^2$, $R^{11}$, $R^{12}$ and $R^{13}$ are identical or different and represent optionally substituted alkyl or alkenyl radicals,
$R^3$ to $R^{10}$ are identical or different and represent hydrogen, or represent optionally substituted alkyl radicals,
and wherein
$R^2$ and $R^3$, together with the atoms to which they are bonded, can also form an optionally substituted monocyclic ring, and
n and m are identical or different and denote 0 or 1, with the proviso that X denotes not represent hydrogen or $R^{13}$ if n and m represent 0, have a potent insect- and mite-repellant action.

The repellent action is considerably better than that of the repellents known from the prior art. The active compounds according to the invention thus represent a useful enrichment of the art.

The present invention thus relates to the use of acrylated α,ω-aminoalcohol derivatives of the general formula I for repelling insects and mites.

The invention furthermore relates to insect- and mite-repellent agents which are characterized in that they contain at least one acrylated α,ω-aminoalcohol derivative of the general formula I.

The agents according to the invention containing at least one derivative of the formula I can also contain other insect repellents. Virtually all the customary repellent are possible here (compare, for example, K. H. Büchel in Chemie der Pflanzenschutz- und Schädlingsbekämpfungsmittel (Chemistry of the Plant Protection Agents and Agents for Combating Pests); published by: R. Wegler, Volume 1, Springer Verlag Berlin, Heidelberg, N.Y., 1970, page 487 et seq.).

In the case of repellent combinations, the acrylated α,ω-aminoalcohols of the general formula I are preferably used together with repellent carboxylic acid amides, 1,3-alkanediols and carboxylic acid esters. Compounds which may be mentioned specifically are 3-methylbenzoic acid diethylamide (DEET), 2-ethyl-hexane-1,3-diol (Rutgers 612) and dimethyl phthalate.

The acylated α,ω-aminoalcohol derivatives which can be used according to the invention are characterized by the general formula (I).

The radicals given in formula (I) preferably have the following meaning:

The alkyl group in the radicals $R^1$ to $R^{13}$ is straight-chain or branched and contains 1 to 12, preferably 1 to 8 and in particular 1 to 6, carbon atoms. Examples which may be mentioned are methyl, ethyl, n- and i-propyl, n-, i- and t-butyl, n-pentyl and n-hexyl.

Optionally substituted alkenyl is straight-chain or branched alkenyl with preferably 2 to 10, in particular 2 to 7, carbon atoms. Examples which may be mentioned are optionally substituted ethenyl, propen-1-yl, propen-2-yl, buten-1-yl, buten-2-yl and buten-3-yl.

The radicals $R^2$ and $R^3$, together with the atoms to which they are bonded, can form 5-to 7-membered saturated rings, which can be substituted by 1 or 2, preferably one, alkyl group, in particular methyl.

The optionally substituted radicals $R^1$ to $R^{13}$ can carry one or more, preferably 1 to 3 and in particular 1 or 2, identical or different substituents. Substituents which may be mentioned are: alkyl with preferably 1 to 10, in particular 1 to 6, carbon atoms, such as methyl, ethyl, n- and i-propyl, n-, i.- and t-butyl, cyclopropyl, and cyclohexyl. Other possible substituents for $R^1$ to $R^{13}$ are, for example, $C_1$–$C_4$-alkoxy, halogen and CN.

Preferably, in the compounds of the general formula (I), one of the indices n and m represents 0 and the other represents 0 or 1, with the proviso that X does not represent hydrogen or $R^{13}$ if n and m represent 0.

Compounds of the general formula (I) which are preferably used as repellents are those in which
X represents hydrogen, $COR^{11}$ or $R^{13}$,
$R^1$ represents $C_1$–$C_7$-alkyl or $C_3$–$C_7$-alkenyl,
$R^2$, $R^{11}$ and $R^{13}$ are identical or different and represent $C_1$–$C_6$-alkyl,
$R^3$–$R^8$ are identical or different and represent hydrogen or $C_1$–$C_6$-alkyl, wherein R$^2$ and R$^3$, together with the atoms to which they are bonded, can also form a 5- or 6-membered monocyclic ring, and n represents 1 and m represents 0.

Compounds of the general formula (I) which are particularly preferably used as repellents are those in which X represents hydrogen or R$^{13}$, wherein R$^{13}$ represents C$_1$-C$_6$-alkyl, R$^1$ represents C$_1$-C$_7$-alkyl or C$_3$-C$_7$-alkenyl, R$_4$ to R$_8$ are identical or different and represent hydrogen or C$_1$-C$_6$-alkyl, R$^2$ and R$^3$, together with the atoms to which they are bonded, form a 5- or 6-membered monocyclic ring, n represents 1 and m represents 0.

Compounds in which R$^1$ represents C$_1$-C$_7$-alkyl or C$_3$-C$_7$-alkenyl, X represents COR$^{11}$ or R$^{13}$, R$^2$ and R$^{11}$ are identical or different and represent C$_1$-C$_6$-alkyl, R$^3$ to R$^8$ are identical or different and represent hydrogen or C$_1$-C$_6$-alkyl, R$^{13}$ represents C$_1$-C$_6$-alkyl, n represents 1 and m represents 0 are furthermore preferred.

Compounds of the general formula (I) which are especially preferred as repellents are those in which m=0 and n=1, R$^1$ represents C$_1$-C$_4$-alkyl, R$^2$, R$^{11}$ and R$^{13}$ are identical or different and represent C$_1$-C$_6$-alkyl, R$^3$ to R$^8$ represent hydrogen and X represents hydrogen, COR$^{11}$ or R$^{13}$, wherein R$^{11}$ and R$^{13}$ have the abovementioned meaning.

Compounds of the general formula (I) which are furthermore especially preferably used as repellents are those in which m=0 and n=1, R$^1$ represents C$_3$-C$_4$-alkyl, R$^2$ and R$^3$, together with the atoms to which they are bonded, form a 6-membered ring, R$^4$ to R$^8$ represents hydrogen and X represents hydrogen or R$^{13}$, wherein R$^{13}$ represents C$_1$-C$_4$-alkyl.

The compounds of the general formula (I) are either known or can be prepared by known methods and processes (compare, for example, Cesare Ferri, Reaktionen der organischen Synthese (Reactions of organic synthesis), Georg Thieme Verlag Stuttgart, 1978, page 223 and page 450).

The compounds of the formula (I) are accordingly obtained by a process in which the α,ω-aminoalcohols, which are known per se or can be prepared by known processes (compared, for example, Cesare Ferri, Reaktionen der org. Synthese (Reactions of organic synthesis), Georg Thieme Verlag Stuttgart, 1978, pages 211 et seq. and 496–497), of the formula (II)

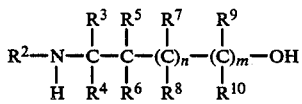

(II)

wherein

R$^2$ to R$^{10}$, n and m have the meaning given under formula (I) are first reacted with carboxylic acid chlorides which are known per se, of the formula (III)

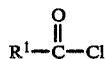

(III)

wherein

R$^1$ has the meaning given under formula (I), if appropriate in the presence of an acid acceptor, such as, for example, triethylamine or potassium carbonate, and if appropriate using a diluent, such as, for example, toluene, CH$_2$Cl$_2$, tetrahydrofuran or acetonitrile, at temperatures between −40° and 110° C.

To prepare compounds of the general formula (I) in which X is other than hydrogen, further acrylation/alkylation is then carried out in a second reaction step, if appropriate after isolation of the intermediate product with the free OH group, with carboxylic acid chlorides which are known per se, of the formula (IV)

R$^{11}$COCl    (IV) to prepare compounds of the formula (I) where X=COR$^{11}$; chlorocarbonic acid esters of the formula (V)

 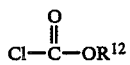

(V)

to prepare compounds of the formula (I) where X=COOR$^{12}$; or alkyl halides of the formula (VI)

R$^{13}$-Y    (VI)

to prepare compounds of the formula (I) where X=R$^{13}$; wherein, in the formula (IV), (V) and (VI), Y represents chlorine, bromine or iodine, preferably bromine or iodine, and R$^{11}$ to R$^{13}$ have the abovementioned meaning, if appropriate in the presence of an acid acceptor, such as, for example, triethylamine or potassium carbonate, or a base, such as, for example, sodium hydride, if appropriate using a diluent, such as, for example, toluene, tetrahydrofuran or acetonitrile, at temperatures between 0° and 110° C. Working up is carried out by customary methods, for example by diluting the reaction mixture with water, extracting the products with methylene chloride or toluene and washing the organic phase with water, drying it and distilling it, or by so-called "incipient distillation", that is to say by prolonged heating to moderately elevated temperatures under reduced pressure, in order to free the products from the last volatile constituents.

Further purification can be carried out by chromatography on silica gel with, for example, hexane: acetone=7:3 as the mobile phase.

The refractive index, melting point, Rf value or boiling point are used to characterize the compounds.

The present invention also relates to new acylated α,ω-aminoalcohol derivatives of the formula

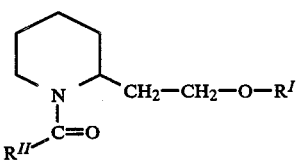

(Ia)

wherein

R$^I$ represents hydrogen, COR$^{11}$, COOR$^{12}$ or R$^{13}$, wherein $R^{11}$, $R^{12}$ and $R^{13}$ are identical or different and represent optionally substituted alkyl or alkenyl radicals and $R^{II}$ represents $C_2$-$C_6$-alkyl, or represents $C_3$-$C_4$-alkenyl Preferred compounds of general formula (Ia) are such wherein $R^I$ represents hydrogen or $R^{13}$ wherein $R^{13}$ stands for an optionally substituted alkyl or alkenyl radical and $R^{II}$ represents $C_2$-$C_6$-alkyl, or represents $C_3$-$C_6$-alkenyl.

The acylated α,ω-aminoalcohol derivatives of the formula

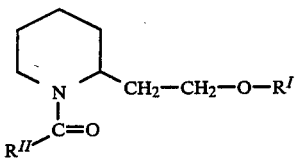
(Ia)

wherein $R^I$ represents hydrogen, $COR^{11}$, $COOR^{12}$ or $R^{13}$, wherein $R^{11}$, $R^{12}$ and $R^{13}$ are identical or different and represent optionally substituted alkyl or alkenyl radicals and $R^{II}$ represents $C_2$-$C_6$-alkyl, or represents $C_3$-$C_6$-alkenyl, are obtained by a process in which the α,ω-aminoalcohol of the formula

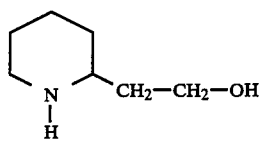
(IIa)

is reacted with a carboxylic acid chloride of the formula

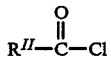
(IIIa)

wherein $R^{11}$ has the abovementioned meaning, if appropriate in the presence of an acid acceptor, such as, for example, triethylamine or potassium carbonate, and if appropriate using an organic diluent, such as, for example, toluene, methylene chloride, tetrahydrofuran or acetonitrile, at temperatures between −40° and 110° C., if appropriate the compounds of the formula

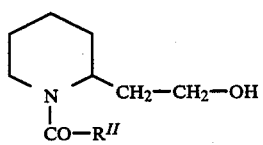
(Ib)

are isolated, and, if appropriate, the further acrylation/alkylation is effected in a second reaction step with carboxylic acid halides which are known per se (in particular carboxylic acid chlorides), of the formula

(IV)

to give compounds of the formula Ia where $R^I$=$COR^{11}$, or with chlorocarbonic acid esters of the formula

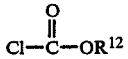
(V)

to give compounds of the formula Ia where $R^I$=$COOR^{12}$, or with alkyl halides of the formula

(VI)

to give compounds of the formula Ia where $R^I$=$R^{13}$, wherein $R^{11}$, $R^{12}$ and $R^{13}$ have the abovementioned meaning and Y represents chlorine, bromine or iodine, preferably bromine or iodine, if appropriate in the presence of an acid acceptor, such as, for example, triethylamine or potassium carbonate, or a base, such as sodium hydride, if appropriate using an organic diluent, such as, for example, toluene, tetrahydrofuran or acetonitrile, preferably at temperatures between 0° and 110° C.

The compounds of the formula (Ia) according to the invention are worked up in a manner analogous to that described above for the preparation of the compounds of the formula (I).

The action of the repellents of the general formula (I) persists for a long time.

They can therefore be used with good success for repelling harmful or troublesome sucking and biting insects and mites.

The sucking insects essentially include the mosquitoes (for example Aedes, Culex and Anopheles species), owl gnats (Phlebotoma), blackfly (Culicoides species), buffalo gnats (Simulium species), biting flies (for example Stomoxys calcitrans), tsetse flies (Glossina species), horseflies (Tabanus, Haematopota and Chrysops species), houseflies (for example Musca domestica and Fannia canicularis), meat flies (for example Sarcophaga carnaria), flies which cause myiasis (for example Lucilia cuprina, Chrysomyia chloropyga, Hypoderma bovis, Hypoderma lineatum, Dermatobia hominis, Oestrus ovis, Gasterophilus intestinalis and Cochliomyia hominovorax), bugs (for example Cimex lectularius, Rhodnius prolixus and Triatoma infestans), lice (for example Pediculus humanus, Haematopinus suis and Damalina oris), Louse flies (for example Melaphagus orinus), fleas (for example Pulex irritans, Cthenocephalides canis and Xenopsylla cheopis) and sand fleas (for example Dermatophilus penetrans).

The biting insects essentially include cockroaches (for example Blatella germanica, Periplaneta americana, Blatta orientalis and Supella supellectilium), beetles (for example Sitophilus granarius, Tenebrio molitor, Dermestes lardarius, Stegobium paniceum, Anobium puntactum and Hylotrupes bajulus), termites (for example Reticulitermes lucifugus) and ants (for example Lasius niger).

The mites include ticks (for example Ornithodorus moubata, Ixodes ricinus, Boophilus microplus and Amblyomma hebreum) and mites in the narrower sense (for example Sarcoptes scabiei and Dermanyssus gallinae).

The active compounds according to the invention, which can be used undiluted or, preferably, in diluted form, can be converted into the formulations customary for repellents. They can in general be used in all the presentation forms customary in cosmetics, for example in the form of solutions, emulsions, gels, ointments, pastes, creams, powders, sticks, sprays or aerosols from spray cans.

For use in the non-cosmetic sector, the active compounds can be incorporated, for example, into granules, oil-based spraying agents or slow release formulations.

The formulations are prepared in a known manner by mixing or diluting the active compounds according to the invention with solvents (for example xylene, chlorobenzenes, paraffins, methanol, ethanol, isopropanol or water), carriers (for example kaolins, aluminas, talc, chalk, highly disperse silicic acid and silicates), emulsifying agents (for example polyoxyethylene fatty acid esters, polyoxyethylene fatty alcohol ethers, alkylsulphonates and acrylsulphonates) and dispersing agents (for example lignin, sulphite waste liquors and methylcellulose).

The active compounds according to the invention can be used in the formulations as mixtures with one another or as mixtures with other known active compounds (for example sunscreen agents). The formulations in general contain between 0.1 and 95% by weight of active compound, preferably between 0.5 and 90%.

For protection from blood-sucking insects or mites, the active compounds according to the invention are either applied to the human or animal skin, or items of clothing and other articles are treated with them.

The active compounds according to the invention are also suitable as an additive to impregnating agents for, for example, textile webs, items of clothing and packaging materials, and as an additive to polishing, cleaning and window-cleaning agents.

The following examples of formulations and the use of the active compounds according to the invention serve for further illustration of the invention.

EXAMPLE 1

A repellent in the form of a lotion for use on the skin is prepared by mixing 30 parts of one of the active compounds according to the invention, 1.5 parts of perfume and 68.5 parts of isopropanol. The isopropanol can be replaced by ethanol.

EXAMPLE 2

A repellent in the form of an aerosol for spraying onto the skin is prepared by formulating 50% of an active compound solution consisting of 30 parts of one of the active compounds according to the invention, 1.5 parts of perfume and 68.5 parts of isopropanol with 50% of Frigen 11/12 (=halogenated hydrocarbon as a propellant gas) as a spray can.

EXAMPLE 3

Another spray can consists of 40% of an active compound solution consisting of 20 parts of one of the active compounds according to the invention, 1 part of perfume and 79 parts of isopropanol and 60% of propane/butane (ratio 15:85).

Individual formulations are prepared according to Examples 1, 2 and 3 using the following active compounds: compounds according to Preparation Examples Nos. 1, 2, 3, 8 and 15.

The following examples of the biological action show the superiority of the substances according to the invention compared with the prior art (diethyltoluamide=DEET):

EXAMPLE A

Repellent test on guineapigs
Test insect: Aedes aegypti (imagines)
Number of test insects: about 5,000
Solvent: Ethanol (99.8%)
3 parts by weight of active compound are taken up in 100 parts by volume of solvent.

A guineapig is shaved on its back over an area of 50 $cm^2$ and is fixed in a narrow cage (box) so that only the shaved area is accessible to mosquitoes. The area is treated with 0.4 ml of active compound solution and, after the solvent has evaporated, the guineapig, together with the box, is placed in a cage measuring 60×60×60 cm containing only the test insects of both sexes fed with sugared water.

The number of mosquitoes which sting the quineapig is observed for 10 minutes. The guineapig is then removed and the test is repeated again after one hour. The experiment is carried out for a maximum of 14 hours, or until the action stops.

In this test, for example, the following compounds from the preparation examples show a superior action compared with the prior art (diethyltoluamide=DEET): (1), (2), (3), (8), (15) and (28).

TABLE A

| Repellent test on guinea pigs | | |
|---|---|---|
| | \multicolumn{2}{c}{Number of stings after:} | |
| Product | $0^h$–$6^h$ | $7^h$–$14^h$ |
| According to the invention: Prep. Ex. No. 1 $\quad$ CH$_3$—C=O, n-C$_4$H$_9$—N—(CH$_2$)$_3$—O—C(=O)—CH$_3$ | 0.1 | 6.3 |
| Prep. Ex. No. 8 $\quad$ CH$_3$—C(CH$_3$)(CH$_3$)—N((CH$_3$)C=O)—(CH$_2$)$_3$—O—C(=O)—CH$_3$ | 1.9 | 3.6 |
| Prep. Ex. No. 2 $\quad$ piperidine with (CH$_2$)$_2$—OH and O=C—C$_4$H$_9$ | 0.1 | 0.6 |
| Prep. Ex. No. 15 $\quad$ n-C$_4$H$_9$—C=O, CH$_3$—N—(CH$_2$)$_3$—O—C(=O)—C$_4$H$_9$(n) | 0.3 | 1.6 |
| Prep. Ex. No. 3 $\quad$ piperidine with (CH$_2$)$_2$—O—CH$_3$ and O=C—C$_4$H$_9$(n) | 0.1 | 3.5 |

TABLE A-continued

Repellent test on guinea pigs

| Product | Number of stings after: 0ʰ-6ʰ | 7ʰ-14ʰ |
|---|---|---|
| Prep. Ex. No. 29 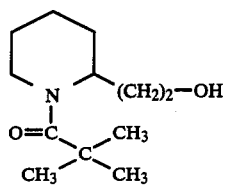 | 0.1 | 2.4 |
| Known: DEET 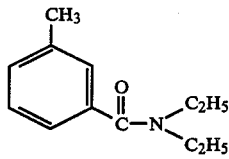 | 2.4 | 11.6 |

Note: "Prep. Ex." denotes "Preparation Example"

EXAMPLE B

Repellent test guineapigs
Test insect: Culex pipiens fatigans
Number of test insects: about 1,000
Solvent: Ethanol (99.8%)
3 parts by weight of active compound are taken up in 100 parts by volume of solvent.

A guineapig is shaved on its back over an area of 50 cm² and is fixed in a narrow cage (box) so that only the shaved area is accessible to mosquitoes. The area is treated with 0.4 ml of active compound solution and, after the solvent has evaporated, the guineapig, together with the box, is placed in a cage measuring 60×60×60 cm containing only the test insects of both sexes fed with sugared water.

The number of mosquitoes which sting the guineapig is observed for 10 minutes.

The guineapig is then removed and the test is repeated again after one hour. The experiment is carried out for a maximum of 10 hours, or until the action stops.

In this test, for example, the following compounds from the preparation examples show a superior action compared with the prior art (diethyltoluamide=DEET): (3), (8), (15), (29).

TABLE B

Repellent test on guinea pigs

| Product | Number of stings after: 0ʰ-6ʰ | 7ʰ-10ʰ |
|---|---|---|
| According to the invention: Prep. Ex. No. 8 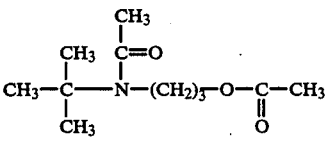 | 0.1 | 3.1 |
| Prep. Ex. No. 15 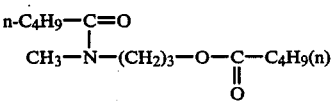 | 0.1 | 2.2 |

TABLE B-continued

Repellent test on guinea pigs

| Product | Number of stings after: 0ʰ-6ʰ | 7ʰ-10ʰ |
|---|---|---|
| Prep. Ex. No. 3 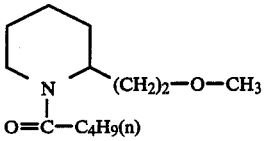 | 0 | 0.6 |
| Prep. Ex. No. 29 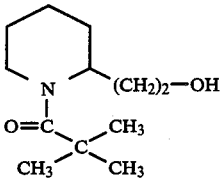 | 0 | 0.2 |
| Known: 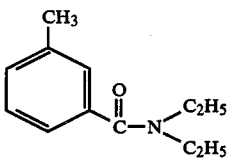 | 0.1 | 4.9 |

Note: "Prep. Ex." denotes "Preparation Example"

Preparation Examples

Preparation Example 1

N,O-Bis-acetyl-N-butyl-1,3-aminopropanol 40 g (0.3 mol) of N-butyl-1,3-aminopropanol and 100 ml of triethylamine (0.72 mol) are dissolved in 1 liter of tetrahydrofuran, and 50 ml of acetyl chloride (0.7 mol) are added at 20° C. The mixture is warmed under reflux for one day and the solid is then filtered off. Methylene chloride is added and the organic layer is washed with water. The organic phase is then dried with magnesium sulphate, the solvent is distilled off on a rotary evaporator and the residue is distilled in a bulb tube oven (boiling point$_{0.6}$ 135°-140° C.). For further purification, the substance is chromatographed over 1 kg of silica gel (mobile phase: cyclohexane:acetone=7:3).
Yield: 52.1 g=81% theory

Preparation Example 2

1-Pentanoyl-2-(2-hydroxyethyl)-piperidine 65 g (0.5 mol) of 2-(2-hydroxyethyl)-piperidine and 90 ml of triethylamine (0.64 mol) are dissolved in 1 liter of tetrahydrofuran, and 80 ml (0.67 mol) of valeryl chloride are added at −20° C. The mixture is warmed at 20° C. for one day and the solvent is then largely removed on a rotary evaporator; the residue is taken up in methylene chloride, the mixture is washed with 1N NaOH solution, the organic phase is dried and the solvent is removed by distillation on a rotary evaporator. In order to remove impurities of the bis-acylated compound, the product is taken up in 200 ml of ethanol and the mixture is warmed at 50° C. with 200 ml of 1N sodium hydroxide solution for one hour. It is evaporated on a rotary evaporator again, the residue is extracted with $CH_2Cl_2/H_2O$, the organic phase is dried and evaporated on a rotary evaporator and the residue is distilled in a bulb tube oven (boiling point$_{0.2}$=165° C).

Yield: 65.4=61% of theory.

Preparation Example 3

1-Pentanoyl-2-(2-methoxethyl)-piperidine 32 g (0.15 mol) of 1-pentanoyl-2-(2-hydroxyethyl)-piperidine are dissolved in 300 ml of tetrahydrofuran, and 5.9 g (0.197 mol) of sodium hydride (80% strength in paraffin) are added at 20° C. The mixture is warmed under reflux for 4 hours and 20 ml of methyl iodide (0.32 mol) are then added to the reaction mixture.

The mixture is then warmed under reflux for 8 hours, 100 ml of ammonium chloride solution are subsequently added at 20° C., the mixture is extracted with methylene chloride and the organic phase is dried with magnesium sulphate and evaported on a rotary evaporator. After purification by chromatography (mobile phase $CH_2Cl_2$:i—$C_3H_7OH$=1:1; silica gel), the product is evaporated on a rotary evaporator and the residue is distilled in an bulb tube oven (boiling point$_{0.2}$: 160° C.).

Yield: 27.7 g=81% of theory.

The further preparation examples listed in the table below were synthesized analogously to the above Preparation Examples 1 to 3.

General formula:

$$\begin{array}{c} R^2 \\ | \\ R^1-N-C(R^3)(R^4)-C(R^5)(R^6)-(C(R^7)(R^8))_n-(C(R^9)(R^{10}))_m-O-X \\ | \\ C=O \end{array} \quad (I)$$

| Prep. Ex. No. | R¹ | R² | R³ | R⁴ | R⁵ | R⁶ | R⁷ | R⁸ | R⁹ | R¹⁰ | n | m | X | physical data ($n_D^{20}$) |
|---|---|---|---|---|---|---|---|---|---|---|---|---|---|---|
| 4 | C₂H₅ | n-C₄H₉ | H | H | H | H | — | — | — | — | 0 | 0 | COOC₂H₅ | 1.455 |
| 5 | CH₃ | n-C₄H₉ | H | H | H | H | — | — | — | — | 0 | 0 | COCH₃ | 1.457 |
| 6 | CH₃ | n-C₄H₉ | H | H | H | H | H | H | — | — | 0 | 1 | COCH₃ | 1.4565 |
| 7 | CH₃ | C₂H₅ | H | H | H | H | H | H | — | — | 1 | 0 | COCH₃ | 1.4532 |
| 8 | CH₃ | t-C₄H₉ | H | H | H | H | H | H | — | — | 1 | 0 | COCH₃ | 1.4565 |
| 9 | CH₃ | n-C₃H₇ | H | H | H | H | H | H | — | — | 1 | 0 | COCH₃ | 1.4540 |
| 10 | CH₃ | CH₃ | H | H | H | H | H | H | — | — | 1 | 0 | COCH₃ | 1.4530 |
| 11 | CH₃ | CH₃ | H | H | H | H | H | H | H | H | 1 | 0 | H | 1.4660 |
| 12 | CH₃ | —(CH₂)₄— | | | H | H | H | H | — | — | 1 | 0 | COCH₃ | 1.4770 |
| 13 | CH₃ | —(CH₂)₄— | | | H | H | H | H | — | — | 1 | 0 | COCH₃ | 1.4780 |
| 14 | CH₃ | i-C₃H₇ | H | H | H | H | H | H | — | — | 1 | 0 | COCH₃ | 1.4549 |
| 15 | CH₃ | CH₃ | H | H | H | H | H | H | — | — | 1 | 0 | CO—C₄H₉—(n) | 1.4526 |
| 16 | n-C₄H₉ | —(CH₂)₄— | | | H | H | H | H | — | — | 1 | 0 | COOC₂H₅ | 1.4650 |
| 17 | n-C₄H₉ | n-C₄H₉ | H | H | H | H | H | H | — | — | 1 | 0 | H | 1.4655 |
| 18 | n-C₄H₉ | n-C₄H₉ | H | H | H | H | H | H | — | — | 1 | 0 | H | 1.4649 |
| 19 | C₂H₅ | —(CH₂)₄— | | | H | H | H | H | — | — | 1 | 0 | H | 1.4960 |
| 20 | CH₃ | —(CH₂)₄— | H | H | H | H | H | H | — | — | 1 | 0 | H | 1.4990 |
| 21 | n-C₃H₇ | —(CH₂)₄— | | | H | H | H | H | — | — | 1 | 0 | H | 1.4905 |
| 22 | n-C₅H₁₁ | —(CH₂)₄— | | | H | H | H | H | — | — | 1 | 0 | CH₃ | 1.4510 |
| 23 | n-C₄H₉ | CH₃ | H | H | H | H | H | H | — | — | 1 | 0 | H | 1.4995 |
| 24 | n-C₄H₉ | —(CH₂)₄— | | | H | H | H | H | — | — | 1 | 0 | C₂H₅ | 1.4730 |
| 25 | n-C₄H₉ | —(CH₂)₄— | | | H | H | H | H | — | — | 1 | 0 | n-C₃H₇ | 1.4711 |
| 26 | n-C₄H₉ | —(CH₂)₄— | | | H | H | H | H | — | — | 1 | 0 | n-C₄H₉ | 1.4713 |
| 27 | n-C₄H₉ | —(CH₂)₃— | | | H | H | H | H | — | — | 1 | 0 | H | 1.4854 |
| 28 | CH₃ | H₃C–C(CH₃)₂–CH₃ (neopentyl type) | | | H | H | H | H | — | — | 1 | 0 | COCH₃ | 1.4625 |
| 29 | t-C₄H₉ | —(CH₂)₄— | | | H | H | H | H | — | — | 1 | 0 | H | 1.4873 |
| 30 | CH(C₂H₅)C₄H₉ | —(CH₂)₄— | | | H | H | H | H | — | — | 1 | 0 | H | 1.4852 |
| 31 | CH₃ | H₃C–C(CH₃)₂–CH₃ (neopentyl type) | | | H | H | H | H | — | — | 1 | 0 | COOC₄H₉ | 1.4588 |
| 32 | CH=CH—C₂H₅ | —(CH₂)₄— | | | H | H | H | H | — | — | 1 | 0 | H | 1.5159 |
| 33 | C(CH₃)=CH—CH₃ | —(CH₂)₄— | | | H | H | H | H | — | — | 1 | 0 | H | 1.5034 |

-continued

General formula:

$$R^2-N(-C(=O)R^1)-C(R^3)(R^4)-C(R^5)(R^6)-(C(R^7)(R^8))_n-(C(R^9)(R^{10}))_m-O-X \quad (I)$$

| Prep. Ex. No. | R¹ | R² | R³ | R⁴ | R⁵ | R⁶ | R⁷ | R⁸ | R⁹ | R¹⁰ | n | m | X | physical data ($n_D^{20}$) |
|---|---|---|---|---|---|---|---|---|---|---|---|---|---|---|
| 34 | CH=CH—CH₃ | —(CH₂)₄— | | H | H | H | H | H | — | — | 1 | 0 | H | 1.5200 |
| 35 | t-C₄H₉ | —(CH₂)₄— | | H | H | H | H | H | — | — | 1 | 0 | H | (−)-Form: [α]₃₆₅ = −127.1° (C = 1.5;THF) |
| 36 | t-C₄H₉ | —(CH₂)₄— | | H | H | H | H | H | — | — | 1 | 0 | H | (+)-Form: [α]₃₆₅ = 125.0° (C = 1.5; THF) |
| 37 | t-C₄H₉ | —(CH₂)₄— | | H | H | H | H | H | — | — | 1 | 0 | COC₄H₉—t | 1.4700 ($n_D^{20}$) |
| 38 | C(CH₃)₂C₂H₅ | —(CH₂)₄— | | H | H | H | H | H | — | — | 1 | 0 | H | 1.4906 ($n_D^{20}$) |
| 39 | C₄H₉ | —(CH₂)₃— | | H | H | H | H | H | — | — | 0 | 0 | COCH₃ | 1.4747 ($n_D^{20}$) |
| 40 | CH₃ | CH₂—CH=CH—CH₃ | H | H | H | H | H | H | — | — | 1 | 0 | COCH₃ | |
| 41 | CH₃ | CH₂—CH=CH—CH₃ | H | H | H | H | H | H | — | — | 1 | 0 | H | |

THF = Tetrahydrofuran

It will be appreciated that the instant specification and claims are set forth by way of illustration and not limitation, and that various modifications are changes may be made without departing from the spirit and scope of the present invention.

What is claimed is:
1. An acrylated α,ω-aminoalcohol derivative of the formula

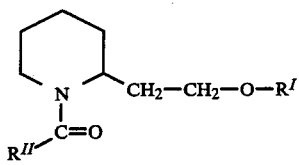

wherein
- $R^I$ represents hydrogen, $COR^{11}$, $COOR^{12}$ or $R^{13}$, wherein
- $R^{11}$, $R^{12}$ and $R^{13}$ are identical or different and represent alkyl containing up to twelve carbon atoms or alkenyl containing up to ten carbon atoms and
- $R^{II}$ represents $C_2$–$C_6$-alkyl, or represents $C_3$–$C_6$-alkenyl.

2. An acylated α,ω-aminoalcohol derivative according to claim 1, wherein
- $R^1$ represents hydrogen or $R^{13}$, wherein
- $R^{13}$ stands alkyl containing up to ten carbon atoms or alkenyl containing up to ten carbon atoms and
- $R^{II}$ represents $C_2$–$C_6$-alkyl, or reprsnts $C_3$–$C_6$-alkenyl.

3. A compound according to claim 1, wherein such compound is 1-pentanoyl-2-(2-hydroxyethyl)-piperidine of the formula

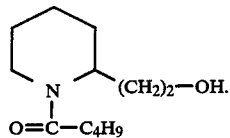

4. A compound according to claim 1, wherein such compound is 1-(dimethylpropionyl)-2-(2-hydroxyethyl)-piperidine of the formula

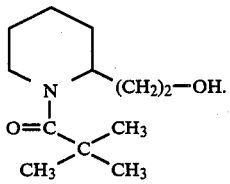

5. An acrylated α,ω-aminoalcohol derivative according to claim 1, wherein $R^1$ represents $COR^{11}$, $COOR^{12}$ or $COOR^{13}$.

6. An insect- and mite-repellent composition comprising an amount effective therefor of a compound according to claim 1 and a diluent.

7. A composition according to claim 6, wherein such compound is 1-pentanoyl-2-(2-hydroxyethyl)-piperidine, or 1-(dimethylpropionyl)-2-(2-hydroxyethyl)-piperidine.

* * * * *

UNITED STATES PATENT AND TRADEMARK OFFICE
CERTIFICATE OF CORRECTION

PATENT NO. : 4,873,252

DATED : October 10, 1989

INVENTOR(S) : Kruger et al.

It is certified that error appears in the above-identified patent and that said Letters Patent is hereby corrected as shown below:

Title Page lines 4-5    [75] Inventors: Correct the last name of the last Inventor to read -- Behrenz --

Col. 17, line 25    After " $R^{13}$ stands " insert -- for --

Signed and Sealed this

Seventh Day of April, 1992

Attest:

HARRY F. MANBECK, JR.

*Attesting Officer*    *Commissioner of Patents and Trademarks*